(12) United States Patent
Alevizos

(10) Patent No.: US 12,427,219 B2
(45) Date of Patent: Sep. 30, 2025

(54) STERILE INDICATOR POUCH

(71) Applicant: Deanna Lynn Alevizos, Farmington, MN (US)

(72) Inventor: Deanna Lynn Alevizos, Farmington, MN (US)

( * ) Notice: Subject to any disclaimer, the term of this patent is extended or adjusted under 35 U.S.C. 154(b) by 761 days.

(21) Appl. No.: 17/651,036

(22) Filed: Feb. 14, 2022

(65) Prior Publication Data
US 2022/0257821 A1   Aug. 18, 2022

Related U.S. Application Data

(60) Provisional application No. 63/200,087, filed on Feb. 12, 2021.

(51) Int. Cl.
| | | |
|---|---|---|
| *A61L 2/28* | (2006.01) | |
| *A61B 50/00* | (2016.01) | |
| *A61B 50/30* | (2016.01) | |

(52) U.S. Cl.
CPC ............ *A61L 2/28* (2013.01); *A61B 50/30* (2016.02); *A61B 2050/002* (2016.02); *A61B 2050/316* (2016.02)

(58) Field of Classification Search
CPC ..... A61L 2/28; A61L 2202/181; A61B 50/30; A61B 2050/002; A61B 2050/316
See application file for complete search history.

(56) References Cited

U.S. PATENT DOCUMENTS

| | | | |
|---|---|---|---|
| 3,991,881 A | 11/1976 | Augurt | |
| 4,091,921 A * | 5/1978 | Lewis | ............... B65D 81/18 |
| | | | 422/26 |
| 5,064,576 A | 11/1991 | Suto | |
| 5,344,017 A | 9/1994 | Wittrock | |
| 7,931,142 B2 * | 4/2011 | Kyritsis | ................. A61B 50/20 |
| | | | 206/440 |
| 9,354,227 B2 | 5/2016 | Bala et al. | |
| D895,136 S | 9/2020 | Whitehead et al. | |
| 2007/0023309 A1 | 2/2007 | Davis | |
| 2009/0123332 A1 * | 5/2009 | Whitehead | ............. B31B 50/74 |
| | | | 422/26 |

(Continued)

FOREIGN PATENT DOCUMENTS

WO   WO2011020185   2/2011

*Primary Examiner* — Nathan J Newhouse
*Assistant Examiner* — Jenine Pagan
(74) *Attorney, Agent, or Firm* — Allison Johnson, P.A.

(57) ABSTRACT

A sterilization pouch that includes a perimeter, a first end, a second end, a length extending from the first end to the second end, a first side, a second side, a width extending from the first side to the second side, a first layer, a second layer bonded to the first layer along a portion of the perimeter to define a pouch having an opening and an interior space for receiving an article therein, a first interior sterilization indicator that changes from a first color state to a second color state when exposed to a sterilization condition, the first interior sterilization indicator being disposed between the first layer and the second layer, being disposed along a major portion of the length of the pouch, being disposed along a major portion of the width of the pouch, or being disposed along both a major portion of the length of the pouch and along a major portion of the width of the pouch, the sterilization indicator being visible through the first layer.

13 Claims, 4 Drawing Sheets

(56) References Cited

U.S. PATENT DOCUMENTS

| | | | |
|---|---|---|---|
| 2010/0108551 A1* | 5/2010 | Kuo | A61L 2/28 206/459.1 |
| 2013/0095336 A1 | 4/2013 | Hermel-Davidock | |
| 2015/0083629 A1 | 3/2015 | Whitehead et al. | |
| 2018/0078665 A1* | 3/2018 | Buccellato | B65D 75/305 |
| 2018/0086903 A1 | 3/2018 | Zhang et al. | |
| 2019/0024137 A1 | 1/2019 | Bala | |
| 2019/0025268 A1 | 1/2019 | Cregger et al. | |

* cited by examiner

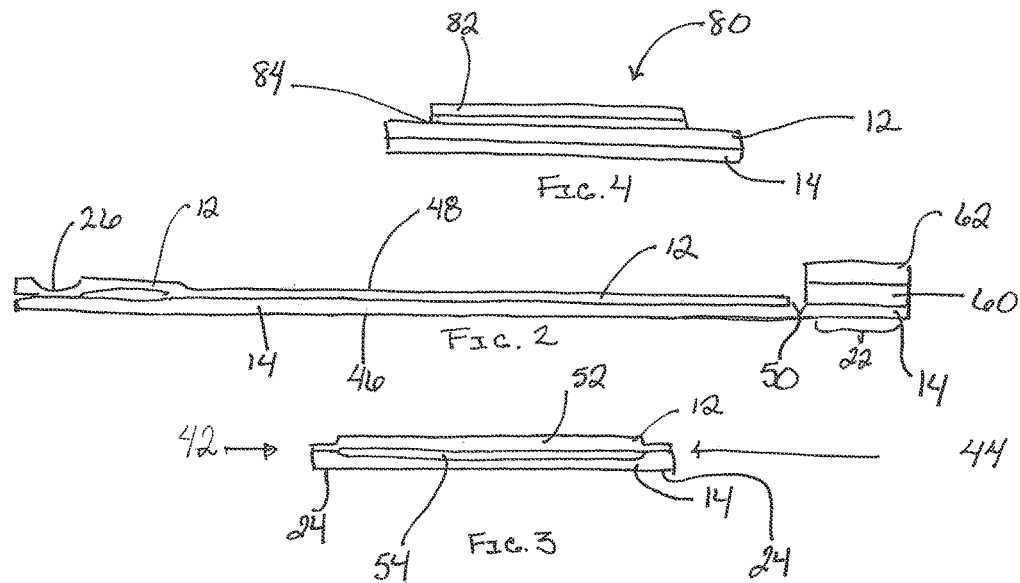
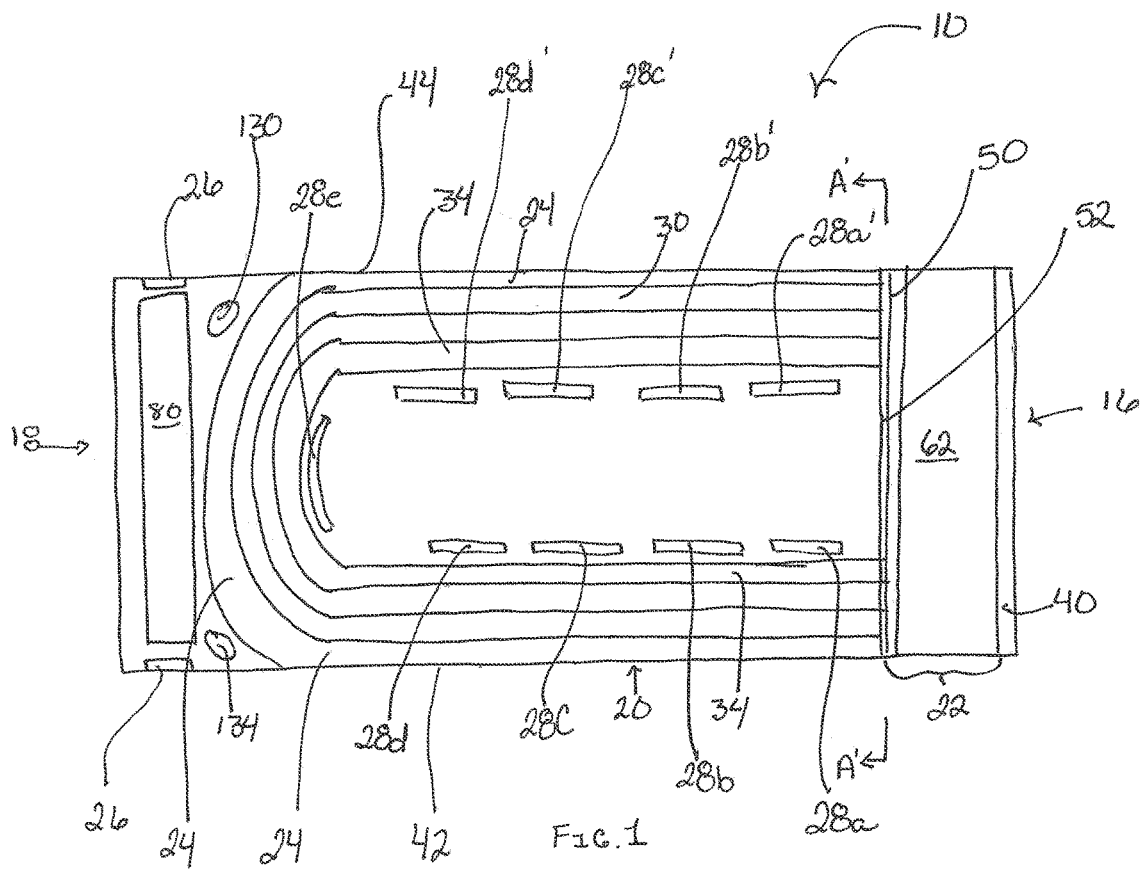

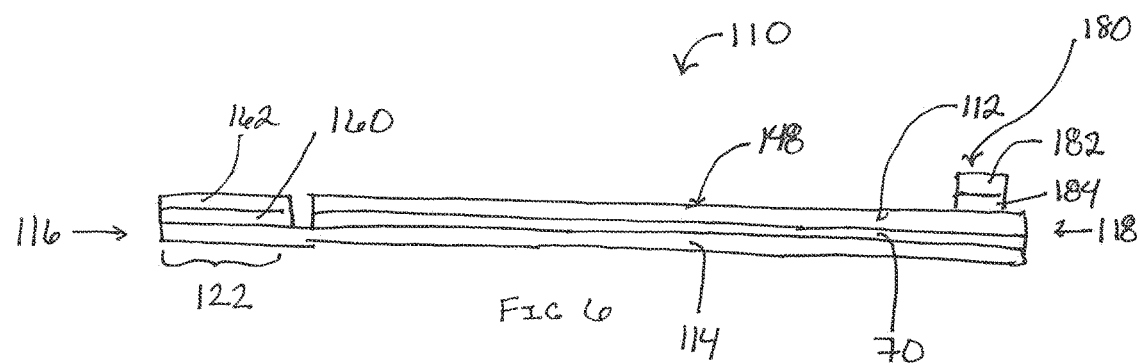
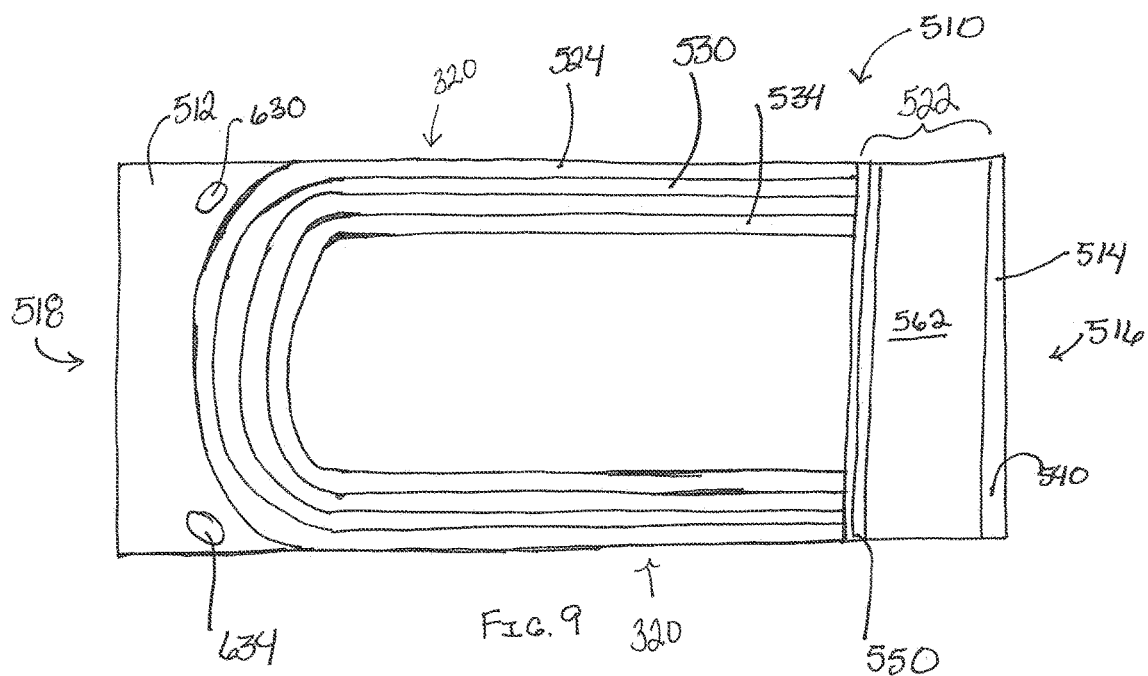

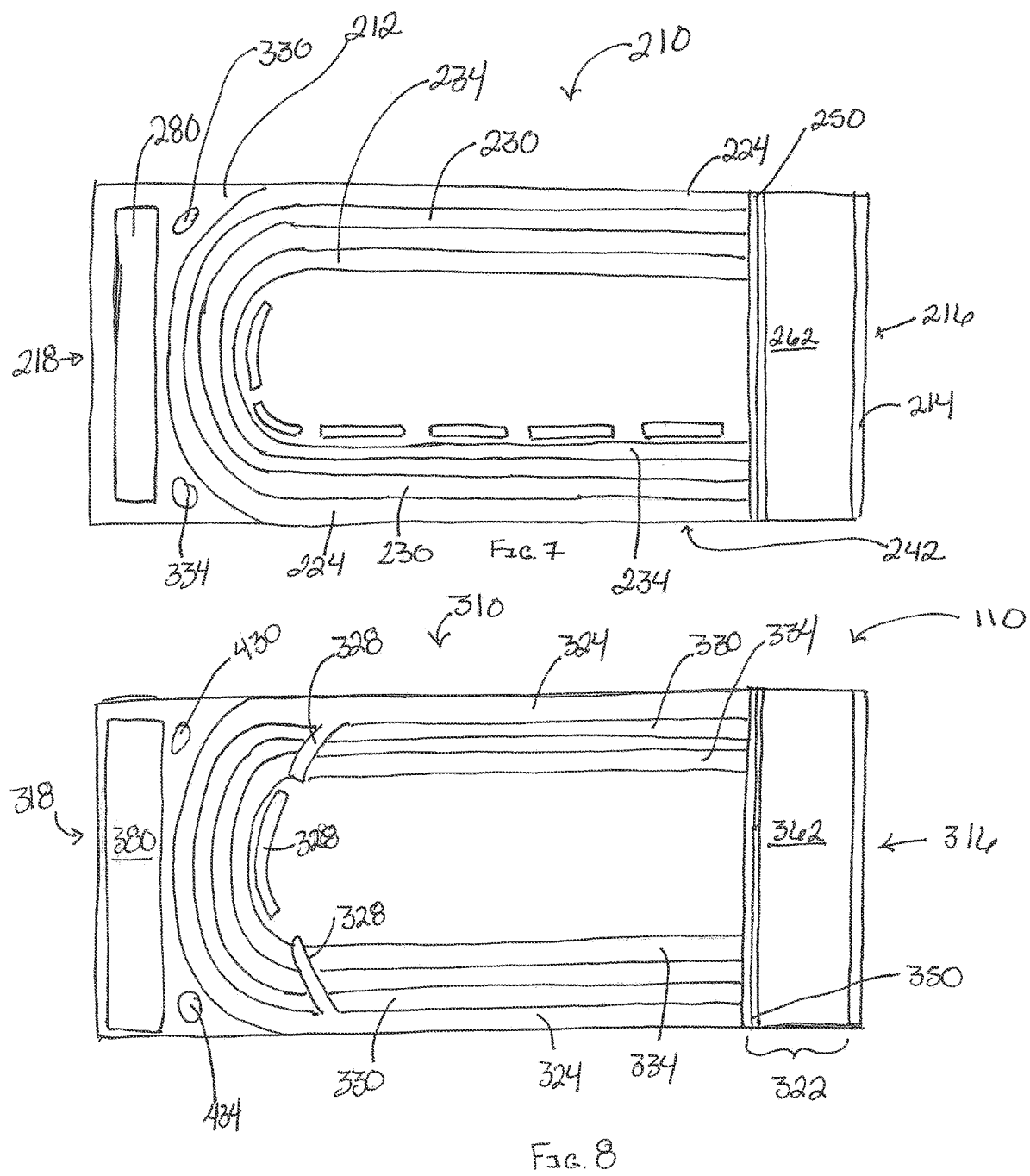

STERILE INDICATOR POUCH

BACKGROUND

The invention is directed to forming sterilization pouches.

Existing sterilization pouches are often formed from a bottom layer that is permeable to the sterilization condition and a top layer that is transparent. The pouch includes at least one indicator that indicates whether or not the sterilization process was successful. The indicators are located in at least two places on the pouch. Typically, there is at least one indicator located within the interior of the pouch and at least one indicator that is located on the exterior of the pouch and is exposed to the environment. The indicator located on the interior of the pouch becomes sealed within the interior of the pouch after the article to be sterilized is placed in the pouch and the pouch is sealed. The indicator on the exterior of the pouch is exposed to the environment and is used to indicate whether or not a sterilization process has occurred. The indicators change from a first color state to a second color state to provide a visual indication that the sterilization process occurred and was successful. The failure of an indicator to change color after a sterilization process indicates that the sterilization process failed.

Steam and high temperatures and pressures are frequently used to sterilize instruments. These conditions can cause the sterilization pouch (e.g., the ends or sides of the sterilization pouch) to curl. The indicators located on the exterior of the pouch and exposed to the environment are often positioned near the end of the pouch. When the ends of the pouch curl, it is often very difficult to see or even notice the indicators, which makes it difficult to determine whether or not the sterilization process was successful, adds to the time it takes to determine whether or not the sterilization process was successful, and creates the potential for errors to occur. It also increases the possibility that a failed sterilization process will go unnoticed.

There is a need for sterilization pouches that include indicators that are readily visible to those who handle the pouch after the sterilization process has occurred.

SUMMARY

In one aspect, the invention features a sterilization pouch that includes a perimeter, a first end, a second end, a length extending from the first end to the second end, a first side, a second side, a width extending from the first side to the second side, a first layer, a second layer bonded to the first layer along a portion of the perimeter so as to define a pouch having an opening and an interior space for receiving an article therein, a first interior sterilization indicator that changes from a first color state to a second color state when exposed to a first sterilization condition, the first interior sterilization indicator being disposed between the first layer and the second layer, disposed along a major portion of the length of the pouch and the width of the pouch, and visible through the first layer.

In one embodiment, the sterilization indicator is disposed on the second layer.

In another embodiment, a portion of the second layer extends past the first layer at the first end, and the portion of the second layer includes an adhesive composition disposed on the second layer, and a removable liner disposed on the adhesive composition.

In other embodiments, the first end includes a sealable flap that includes the first layer, an adhesive composition disposed on the first layer, and a removable liner disposed on the adhesive composition.

In some embodiments, the sterilization indicator is linear. In other embodiments, the sterilization indicator comprises at least two different sterilization indicators.

In one embodiment, the sterilization indicator includes at least two different sterilization indicators in the form of substantially parallel lines. In another embodiment, the sterilization indicator includes at least two different sterilization indicators in the form of parallel lines positioned near the first side and near the second side.

In other embodiments, the sterilization pouch further includes a top and a bottom, the sterilization indicator being visible from the exterior of the pouch when viewed from the top of the pouch.

In some embodiments, further the sterilization pouch further includes a top, a bottom, and a second sterilization indicator disposed on the bottom of the pouch, the first sterilization indicator being visible from the exterior of the pouch when viewed from the top of the pouch, and the second sterilization indicator being visible from the exterior of the pouch when viewed from the bottom of the pouch.

In another embodiment, the sterilization pouch further includes barriers positioned interior to and adjacent the first indicator. In other embodiments, the pouch further includes barriers positioned interior to and adjacent the first indicator and generally defining a discontinuous U shape.

In some embodiments, the pouch further includes a second sterilization indicators and further includes barriers positioned interior to and adjacent the second indicator and generally defining a discontinuous U shape.

In other embodiments, the pouch includes two sterilization indicators (a first and a second sterilization indicator) and the first and second indicators define an arcuate pattern near the second end of the pouch and the pouch further includes an arcuate barrier disposed interior to and adjacent the arcuate pattern of indicators.

In another aspect, the invention features a sterilization pouch that includes a perimeter, a first end, a second end, a length extending from the first end to the second end, a first side, a second side, a width extending from the first side to the second side, a first layer, a second layer bonded to the first layer along a portion of the perimeter so as to define a pouch having an opening and an interior space for receiving an article therein, a first interior sterilization indicator that changes from a first color state to a second color state when exposed to a first sterilization condition, a second interior sterilization indicator that changes from a first color state to a second color state when exposed to a second sterilization condition, the first and second interior sterilization indicators being disposed between the first layer and the second layer, disposed along a major portion of the length of the pouch and the width of the pouch, and visible through the first layer, and barriers positioned interior to and adjacent at least one of the first indicator and the second indicator. In one embodiment, the barriers define a discontinuous pattern. In another embodiment, the pouch further includes a barrier that extends over at least one of the first and second indicators.

In other aspects, the invention features a sterilization pouch that includes a perimeter, a first end, a second end, a length extending from the first end to the second end, a first side, a second side, a width extending from the first side to the second side, a first layer, a second layer bonded to the first layer along a portion of the perimeter so as to define a pouch having an opening and an interior space for receiving an article therein, a first interior sterilization indicator that changes from a first color state to a second color state when exposed to a first sterilization condition, a second interior sterilization indicator that changes from a first color state to a second color state when exposed to a second sterilization condition, the first and second interior sterilization indicators being disposed between the first layer and the second layer, disposed along a major portion of the length of the pouch, and visible through the first layer, and barriers positioned interior to and adjacent at least one of the first indicator and the second indicator, the barriers being positioned along a major portion of the length of the pouch, along a major portion of the width of the pouch, or a combination thereof.

The invention features a sterilization pouch that includes at least one indicator that is readily visible to those who handle the pouch after the sterilization process has occurred.

Other features and advantages will be apparent from the following description of the preferred embodiments, the detailed description, upon reference to the drawings, and from the claims.

Glossary

In reference to the invention, these terms have the meanings set forth below:

The term "major portion" means greater than 50%.

BRIEF DESCRIPTION OF THE DRAWINGS

FIG. 1 is a top view of a sterilization pouch;
FIG. 2 is a side view of the sterilization pouch of FIG. 1;
FIG. 3 is a cross sectional view of the sterilization pouch of FIG. 1 taken along line A'-A';
FIG. 4 is an end view as seen from one end of the sterilization pouch of FIG. 1;
FIG. 6 is a side view of a sterilization pouch in accordance with another embodiment;
and
FIG. 7 is a top view of a sterilization pouch in accordance with another embodiment.
FIG. 8 is a top view of a sterilization pouch in accordance with another embodiment.
FIG. 9 is a top view of a sterilization pouch in accordance with another embodiment.

DETAILED DESCRIPTION

Figure 5:
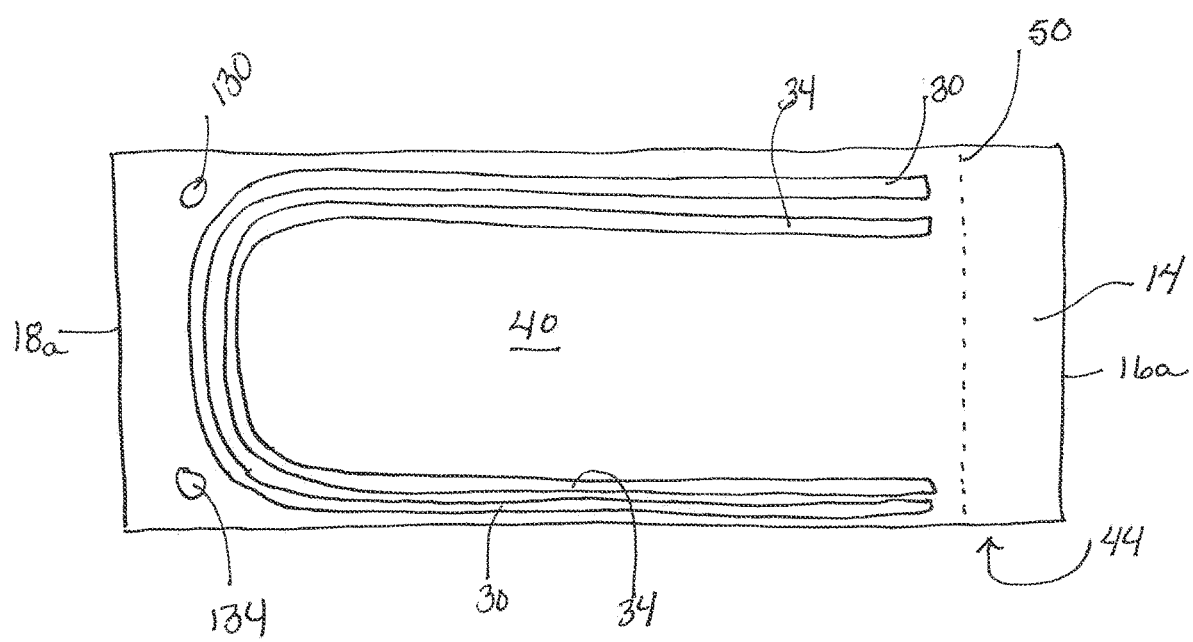
FIG. 5 is a top view of the bottom layer of the sterilization pouch of FIG. 1.

The sterilization pouch includes a top layer, a bottom layer, and two sterilization indicators that are disposed along a major portion of a longitudinal extent of the interior of the pouch, are exposed to the sterilizing environment within the pouch enclosure when the pouch is sealed, and are visible through the top layer of the pouch (e.g., when viewed from the top of the pouch). At least one of the top and bottom layers is sufficiently porous to both permit a sterilization medium to sterilize an article enclosed within the pouch and preclude entry of microorganisms therein.

Referring now to the drawings, in which like numerals represent like components throughout the several views, the preferred embodiments are next described. The following description of preferred embodiments is merely exemplary in nature and is in no way intended to limit the invention, its application, or uses.

Referring to FIGS. 1-5, the sterilization pouch 10 includes a top layer 12, a bottom layer 14, a first end 16, a second end 18, a perimeter 20, a foldable sealing flap 22 at the first end 16, a seal 24 extending along a major portion of the perimeter 20 of the sterilization pouch 10, a first sterilization indicator 30, a second sterilization indicator 34, and an opening 54 defined by the top layer 12 and the bottom layer 14 and originating at the first end 52 of the top layer 12. The sterilization pouch 10 also includes a first corresponding exterior sterilization indicator 130 and a second corresponding exterior sterilization indicator 134.

The bottom layer 14 is sealed to the top layer 12 at the perimeter seal 24 and also at points 26. The bottom layer 14 includes an interior surface 40 in facing relationship with the interior surface of the top layer 12 and an exterior surface 46 exposed to the environment. The bottom layer 14 also includes the first sterilization indicator 30, which is disposed on (e.g., printed on) the interior surface 40 of the bottom layer 14, and the second sterilization indicator 34, which is disposed on (e.g., printed on) the interior surface 40 of the bottom layer 14. The indicators 30, 34 are in facing relation to the interior surface of the top layer 12. The first corresponding exterior indicator 130 is also disposed on the top surface 40 of the bottom layer 14. The first corresponding exterior indicator 130 is positioned exterior to the interior of the pouch and is compositionally the same as the first sterilization indicator 30 located on the interior of the pouch 10. The second corresponding exterior indicator 134 is also disposed on the top surface 40 of the bottom layer 14. The second corresponding exterior indicator 134 is located at a second position on the top surface 40 of the bottom layer 14 of the pouch 10 at a position that is exterior to the interior of the pouch and is compositionally the same as the second sterilization indicator 134 located on the interior of the pouch 10. It is to be understood that the locations of each of the interior sterilization indicators can be interchanged; similarly, the locations of each of the exterior sterilization indicators can be interchanged. One exterior/interior indicator pair (e.g., interior indicator 30 and corresponding exterior indicator 130) can each be responsive to steam sterilization, and the other exterior/interior indicator pair (e.g., interior indicator 34 and corresponding exterior indicator 134) can each be responsive to gas sterilization (e.g., ethylene oxide) or vice versa. The pouch can thus be seen to include first and second indicator pairs, one of which is an indicator for indicating the results of a steam sterilization process, and the other of which is an indicator for indicting the results of a gas sterilization process.

The first and second sterilization indicators 30, 34 are in a continuous pattern of two adjacent spaced apart U shapes that follow the perimeter seal 24 from the first end 16 to the second end 18 and back to the first end 16. The first and second sterilization indicators 30, 34 are positioned interior to and adjacent the perimeter seal 24. Each of the first and second sterilization indicators 30, 34 are responsive to at least one sterilization process and undergo a visually perceptible change in color to indicate that successful sterilization has occurred at the indicator. The sterilization indicators 30, 34 can be of any suitable shape, dimension and form and preferably extend along a major portion of at least one side, at least one end of the pouch or a combination thereof. Although the sterilization indicators 30, 34 are illustrated as being continuous, they can also be discontinuous. Preferably the sterilization indicators 30, 34 extend along a major portion of the longitudinal extent of the pouch (e.g., extending along the longitudinal extent of the first side 42 from near the first end 16 of the first side 42 to near the second end 18 of the first side 42 of the pouch, extending along the longitudinal extent of the second side 44 from near the first end 16 of the second side 44 to near the second end 18 of the second side 44 of the pouch, or extending along both longitudinal extents), a major portion of the width of the pouch (e.g., extending from near the perimeter seal 24 at the first side 42 to near the perimeter seal 24 at the second side 44 of the pouch), or along both a major portion of the longitudinal extent of the pouch and a major portion of the width of the pouch.

A discontinuous series of barriers 28 are positioned interior to and adjacent the first and second indicators 30, 34. The series of barriers follows the U shaped pattern of the sterilization indicators 30, 34 along the longitudinal extent of a first side 42 of the pouch (i.e., barriers 28a-28d), generally across the width of the pouch generally following along the curved end portion of the indicators 30, 34 (i.e., barrier 28e), and along the longitudinal extent of a second side 44 of the pouch (i.e., barriers 28a'-28d'). The barriers 28 are defined by regions of the top layer 12 that are sealed to the bottom layer 14. The barriers 28 serve as impediments to the movement of the article to be sterilized. The barriers 28 can impede or prevent articles that have been inserted into the pouch from moving into the area of the indicators and partially or completely covering or obstructing all or a portion of the indicators from view. The barriers thus can assist in maintaining the visibility of the indicators such that after a sterilization process has been completed, the indicators are clearly and readily visible to the user. The barriers thus can assist in enabling a user to rapidly conduct a visual inspection of the pouch to determine whether or not the sterilization process has been successful.

One end 16, the pouch 10, as illustrated, includes an optional predetermined fold line 50 in the bottom layer 14, which can be used to facilitate folding of the foldable sealing flap 22 onto the exterior surface 48 of the top layer 12. The foldable sealing flap 22 is defined by the portion 22 of the bottom layer 14 that extends beyond the first end 52 of the top layer 12. An adhesive composition 60 is disposed on the bottom layer 14 in the area of the flap 22 and a release liner (e.g., release paper) 62 is disposed on the adhesive composition 60 to cover the adhesive composition until use. The release liner 62 is removable from the adhesive composition 60 and, when removed, the exposed adhesive composition 60 can be used to adhere the interior surface 40 of the bottom layer 14 to the exterior surface 48 of the top layer 12, to thereby define an interior space, and to seal the interior space of the pouch 10 from the environment. An article (e.g., an instrument) to be sterilized can be inserted into the pouch 10 through the opening 52 formed between the top 12 and bottom 14 layers near the first end 16 of the pouch 10. In use, the release liner 62 can be removed from the adhesive composition 60, the flap 22 can be folded over onto the exterior surface 46 of the top layer 12 of the pouch 10, and the adhesive 60 can be pressed against the exterior surface 46 of the top layer 12 to seal the pouch 10 and form an interior sealed space.

At the opposite end 18 of the pouch 10, the top layer 12 is sealed to the bottom layer 14 at two points 26. The two seal points 26 maintain the top layer 12 in a fixed position relative to the bottom layer 14 but also enable the free portions of the top layer 12 and bottom layer 14 to be peeled away from each other. After the sterilization process, this feature enables the two layers 12, 14 to be easily separated from one another, which provides an easy way to open the pouch and release any contents (e.g., sterilized articles) within the pouch.

In the embodiment shown in FIGS. 1-5, the pouch additionally includes an optional dedicated area 80 for receiving information. In FIGS. 1-5, the dedicated area 80 (e.g., a matte surface) is in the form of an ink-receiving surface on which information can be placed (e.g., written with ink, printed with ink, applied as a label, and combinations thereof). The dedicated area 80 can include a separate layer 82 adhered to the top layer 12 of the pouch 10 through an adhesive composition 84. Alternatively, the dedicated area 80 can be the result of a process that alters the surface properties of the top layer 12 such that it can receive and maintain information in a variety of forms including, e.g., ink (e.g., handwritten or printed information including such information as dates, times and conditions), adhesive labels, and combinations thereof.

The seal around a major portion of the perimeter of the pouch (i.e., the perimeter seal 24) is defined by the top layer sealed (e.g., heat sealed, adhered, or a combination thereof) to the bottom layer. The seal can be formed by heat sealing according to a variety of processes including, e.g., hot bar sealing, impulse heating, hot air blast sealing, ultrasonic sealing and combinations thereof. Alternately or in addition, the top layer can be adhered to the bottom layer through an adhesive composition. FIG. 6 is a side view of an embodiment of a sterilization pouch 110 that includes an adhesive layer (e.g., an adhesive composition) 70 disposed between the top layer 112 and the bottom layer 114 such that the top layer 112 is bonded to the bottom layer 14 through the adhesive layer 70 along a major portion of the perimeter of the pouch 110. Also shown are the first end 116, second end 118, foldable sealing flap 122, which includes adhesive composition 160 and release liner 162, label 180, which includes a substrate 182 adhered to the exterior surface 148 of the top layer 112 through adhesive composition 184.

The sterilization pouches can be constructed for use in a variety of sterilization processes including, e.g., steam, ethylene oxide, hydrogen peroxide, electron beam radiation, gamma radiation, ultraviolet light radiation, and combinations thereof. One useful steam sterilization process condition that will cause a complete color change that corresponds to successful sterilization includes exposing the package to steam at 250° F. (121° C.) for 10 minutes. Other useful steam sterilization conditions include, e.g., exposure to steam for from 4 minutes to 5 minutes at 272° F. (133° C.) or even for 20 minutes at 250° F. (121° C.). The sterilization indicator for the steam sterilization process may exhibit some color change after longer periods of exposure to the steam at temperatures below 250° F. (121° C.), or even after shorter periods of exposure to the steam at temperatures greater than 250° F. (121° C.).

One useful ethylene oxide sterilization process condition that will cause a complete color change that corresponds to successful sterilization includes exposing the package to ethylene oxide at 8 psi and 135° F. (57° C.) for 60 minutes. Another useful ethylene oxide sterilization condition includes exposure to from 600 milligrams (mg) to 700 mg of ethylene oxide per liter of sterilizing volume at 130° F. and 50% relative humidity for about 105 minutes. The sterilization indicator for the ethylene oxide sterilization process may exhibit some color change with extended exposure to the ethylene oxide at ambient room temperatures, or even after exposure to the ethylene oxide in as little as 15 minutes if the temperature and pressure are elevated, or even after exposure to the ethylene oxide at pressures as low as normal atmospheric ambient pressures for greater periods of time and at elevated temperatures. When the pouch is subjected to incomplete or insufficient sterilization process conditions, the internal indicators will not change to the color that indicates successful sterilization.

The components of the sterilization pouch can be manufactured from a variety of compositions and materials. As to the sterilization indicator, for example, any suitable sterilization indicator can be incorporated into the pouch. Useful sterilization indicators include chemical sterilization indicator compositions (e.g., inks) designed to react to a specific sterilization process or processes including, e.g., steam, ethylene oxide, formaldehyde, gas plasma (e.g., hydrogen peroxide), dry heat, irradiation (e.g., ultra violet light radiation, gamma radiation, and electron beam radiation), and combinations thereof. The chemical sterilization indicator preferably meets the criteria specified under various standards set by various standard setting bodies including, e.g., standard ANSI/AAMI/ISO 11140-1:2014 "Sterilization of Healthcare Products—Chemical Indicators—Part 1: General Requirements" (Arlington, Virginia: AAMI, 2014), The International Organization for Standardization (ISO), and the European Committee for Standardization (CEN). Useful chemical sterilization indicator compositions include, e.g., solvent-based compositions (e.g., polar solvent based inks) and water-based compositions (e.g., inks). Solvent based inks are particularly useful for printing on polymer film substrates. Water based inks are particularly useful for printing on paper substrates.

In one embodiment, at least one indicator is a steam sterilization indicator. The steam sterilization process indicator changes color from one designated initial color (e.g., light blue) to another, readily distinguishable color (e.g., dark blue) upon sufficient exposure to complete sterilization conditions. The color change to the desired ending color can be caused by a chemical reaction in the ink. One useful chemical reaction includes a copper or lead compound reacting with a source of sulfur to produce copper or lead sulfide, which results in a visual color change. In another embodiment, at least one sterilization indicator is an ethylene oxide sterilization indicator (i.e., the indicator is indicative of successful sterilization by ethylene oxide). A useful ethylene oxide sterilization indicator changes color from one designated initial color (e.g., a blue/grey) to another designated, readily distinguishable color (e.g., a gold/brown). The color change from the initial blue/grey color to the sterilization gold/brown color can be achieved using a pyridine derivative that becomes acetylated when reacted with ethylene oxide.

Steam sterilization indicator compositions are described in a variety of US patents and published applications including, e.g., US 2019-0008990, US 2014-0370604, U.S. Pat. Nos. 5,916,816, and 9,176,103. One class of useful steam sterilization indicator compositions includes, e.g., an organic Bi(III) compound, a sulfur source, a carbonate salt, and strontium hydroxide. One class of solvent-based steam sterilization indicator compositions includes, e.g., bismuth oxychloride or bismuth subcarbonate, a sulfur source, and a compound capable of generating alkaline conditions when exposed to steam (e.g., carbonate salts). Another class of solvent-based steam sterilization indicator compositions includes, e.g., a bismuth oxide or an organic bismuth compound, a sulfur source, and a compound that makes the composition alkaline when exposed to water vapor at an elevated temperature (e.g., a carbonate salt).

One class of useful water-based chemical indicators for use in ethylene oxide sterilization processes is disclosed in US 2004-0241862 (Puntambekar). These chemical indicators include a pH indicator dye (e.g., Bromocresol green, Bromophenol blue, Methyl red, Ethyl orange, and combinations thereof), optionally a polymer, optionally a crystallized hexahydrate metal salt, and optionally an acidic compound. Other classes of chemical indicators for use in ethylene oxide sterilization processes are disclosed in U.S. Pat. Nos. 3,098,751, and 2,998,306.

Another class of chemical indicator compositions includes a reactive composition adhered to a substrate. The reactive composition includes a transition metal reagent, an oxidizing agent, and a carrier or binder. Useful transition metal reagents include, e.g., iron, copper, nickel, manganese, molybdenum, zinc, titanium, vanadium, silver, cobalt, platinum, and combinations thereof. Specific examples of useful transition metal reagents include, e.g., potassium ferricyanide, Prussian blue, Turnbull blue, potassium iron (III) hexacyanoferrate, sodium ferricyanide, and combinations thereof. Useful oxidizing agents include, e.g., potassium dichromate, sodium dichromate, potassium permanganate, and combinations thereof. Useful classes of carriers include, e.g., resins (e.g., gum Arabic, gum ghatti, guar gum, locust (carob)bean gum, karaya gum, gum tragacanth, chicle, rosin ester, tall oil, manila copais, corn gluten, coumarone-indene resin, crown gum, damar gum, polydimethylstyrene, gum elemi, *galbanum* resin, gellan gum, ghatti gum, gluten gum, gualac gum, guarana gum, heptyl paraben, cellulose resin, mastic gum, oat gum, opopanax gum, terpene resin, turpentine gum, zanthan gum, zein, and combinations thereof), rosins (e.g., rosin glycerol ester, rosin adduct with fumaric acid and pentaerythritol ester, gum rosin, wood rosin, glycerol ester rosin, gum or wood pentaerythritol ester, partially hydrogenated glycerol ester rosin, partially hydrogenated pentaerythritol ester rosin, partially hydrogenated methyl ester rosin, partially dimerized glycerol ester rosin, tall oil rosin, and combinations thereof), polymers (e.g., ethylene vinyl acetate, polyamide, ethylene oxide polymer, ethylene oxide/propylene oxide copolymer, isobutylene-isoprene copolymer, polyacrylamide, polylimonene, polyisobutylene, polymaleic acid, polypropylene glycol, polyvinyl acetate, polyvinyl alcohol, polyvinyl polypyrrolidone, shellac, polystyrene, styrene terpolymer, styrene copolymer, sucrose acetate isobutyrate, polyvinylidene chloride, and combinations thereof.

The indicator composition can be printed on the bottom layer or the top layer or both using any suitable process including, e.g., flexographic, gravure, screen printing (e.g., serigraph) processes, and combinations thereof.

The bottom layer of the pouch preferably is porous to sterilization gases such as steam and ethylene oxide. Useful bottom layers include, e.g., cellulose fibers, paper (e.g., Kraft paper and medical grade paper), polymers (e.g., polylactide, polyglycolic acid, polyacrylic acid, polycaprolactone, polyurethane, polyethylene glycol, polyethylene-poly(ethylene oxide) copolymers, polyethylene-poly(ethylene oxide) amphiphilic graft copolymers, and combinations thereof), polymeric fibers, TYVEK nonwoven webs (e.g., medical grade TYVEK and nonwoven polyolefin webs), direct seal papers, and combinations thereof. The bottom layer optionally is treated with a coating (e.g., a sizing) to improve its adhesion to the top layer of the pouch.

The top layer of the pouch preferably is transparent or sufficiently transparent to enable the indicators to be viewed through the top layer. Suitable top layers include, e.g., single and multilayer polymer films (e.g., core layers, tie layers (e.g., ethylene vinyl alcohol), and sealant skin layers) derived from a variety of polymers and polymer film layers including, e.g., polyolefin (e.g., polyethylene (e.g., low density polyethylene, linear low density polyethylene, high density polyethylene, and combinations thereof), polypropylene (isotactic polypropylene high crystallinity polypropylene, low crystallinity polypropylene, isotactic/syndiotactic polypropylene and combinations thereof), ethylene/propylene copolymers, polybutene-1, ethylene/propylene/butene terpolymers, and combinations thereof), polyesters (e.g., polyethylene terephthalate, polybutylene terephthalate, and combinations thereof), polycarbonate, polystyrene, styrene-butadiene copolymers, styrene-butadiene-styrene terpolymers, polyacrylamide, polymethacrylate, poly(methyl)methacrylate, polyimide, polyamide, polyvinylchloride, ethylene acrylic acid, ethylene methacrylic acid, and combinations thereof.

Other embodiments are within the claims. Although the sterilization indicators have been depicted as being disposed on the interior surface of the bottom layer, alternatively or in addition, the sterilization indicators can be disposed on the interior surface of the top layer.

Although the barriers 28 have been depicted as following the general path of the indicators, the barriers are optional and can be of any suitable configuration. In FIG. 7 an embodiment of the sterilization pouch 210 is shown that includes a series of barriers 228 positioned interior to and adjacent the first and second sterilization indicators 230, 234 along one side 242 of the pouch 210. The series of barriers 228 follow a portion of the U shaped pattern of the indicators 230, 234 along the longitudinal extent of a first side 242 of the pouch (i.e., barriers 228a-228d) and along the curved end portion of the pouch (i.e., barriers 228e and 228e'). The barriers 228 are defined by regions of the top layer 212 sealed to the bottom layer 214.

In FIG. 8 an embodiment of the sterilization pouch 310 is shown in which an series of barriers 328 extend in a curve along the end portion 318 of the pouch 310, interior to and adjacent the first and second indicators 330, 334 present at the curved end portion 318 of the pouch 310. The sterilization pouch 310 includes a first end 316, a second end 318, a perimeter 320, a foldable sealing flap 322 at the first end 316, and a perimeter seal 324 extending along a major portion of the perimeter 320 of the sterilization pouch 310. The sterilization pouch 310 also includes a first corresponding exterior sterilization indicator 430 and a second corresponding exterior sterilization indicator 434. As indicated above, it is to be understood that the locations of each of the interior sterilization indicators can be interchanged; similarly, the locations of each of the exterior sterilization indicators can be interchanged.

In FIG. 9 an embodiment of the sterilization pouch 510 includes a top layer 512, a bottom layer 514, a foldable sealing flap 522 at the first end 516, a perimeter seal 524 extending along a major portion of the perimeter 320 of the sterilization pouch 510, a first sterilization indicator 530, and a second sterilization indicator 534. The bottom layer 514 is sealed to the top layer 512 at the perimeter seal 524. The first and second sterilization indicators 530, 534 are in the pattern of two adjacent spaced apart U shapes that follow the perimeter seal 524 from the first end 516 to the second end 518, across the width of the pouch, and back to the first end 516. The sterilization pouch 510 also includes a first corresponding exterior sterilization indicator 630 and a second corresponding exterior sterilization indicator 634. The first corresponding exterior indicator 630 is located at a first position on the interior surface 540 of the bottom layer 514 and exterior to the interior of the pouch and is compositionally the same as the first sterilization indicator 530 located on the interior of the pouch 510. The second corresponding exterior indicator 634 is located at a second position on the interior surface 540 of the bottom layer 514 and exterior to the interior of the pouch and is compositionally the same as the second sterilization indicator 534 located on the interior of the pouch 510. As set forth above, it is to be understood that the locations of each of the interior sterilization indicators can be interchanged; similarly, the locations of each of the exterior sterilization indicators can be interchanged. One exterior/interior indicator pair (e.g., interior indicator 530 and corresponding exterior indicator 630) can each be responsive to steam sterilization, and the other exterior/interior indicator pair (e.g., interior indicator 534 and corresponding exterior indicator 634) can each be responsive to gas sterilization (e.g., ethylene oxide). The pouch 510 can thus be seen to include first and second indicator pairs, one of which is an indicator for indicating the results of a steam sterilization process, and the other of which is an indicator for indicting the results of a gas sterilization process.

The patents and publications referenced herein are incorporated herein to the extent they do not conflict with other statements within this application.

What is claimed is:

1. A sterilization pouch comprising:
a perimeter;
a first end;
a second end;
a length extending from the first end to the second end, the length having a major portion;
a first side;
a second side;
a width extending from the first side to the second side, the width having a major portion;
a first layer having a top exterior facing surface and a bottom interior facing surface;
a second layer bonded to the first layer along a portion of the perimeter so as to define a pouch having an opening and an interior space for receiving an article therein, the second layer having a top interior surface and a bottom exterior surface;
a first interior sterilization indicator that changes from a first color state to a second color state when exposed to a first sterilization condition, the first interior sterilization indicator
being disposed between the first layer and the second layer,
extending along the major portion of the length of the pouch and extending along the major portion of the width of the pouch, and
being visible through the first layer; and
a second interior sterilization indicator different from the first interior sterilization indicator, the first and second sterilization indicators being in the form of parallel lines positioned near the first side of the pouch and near the second side of the pouch, each interior sterilization indicator defining a U shape.

2. The sterilization pouch of claim 1, wherein the first interior sterilization indicator is disposed on the second layer.

3. The sterilization pouch of claim 1, wherein a portion of the second layer extends past the first layer at the first end, and the portion of the second layer comprises
an adhesive composition disposed on the second layer, and
a removable liner disposed on the adhesive composition.

4. The sterilization pouch of claim 1, wherein the first end comprises a sealable flap comprising the first layer, an adhesive composition disposed on the first layer, and a removable liner disposed on the adhesive composition.

5. The sterilization pouch of claim 1, wherein the first interior sterilization indicator is linear.

6. The sterilization pouch of claim 1, wherein the second interior sterilization indicator changes from a first color state to a second color state when exposed to a second sterilization condition.

7. The sterilization pouch of claim 1 further comprising a top and a bottom opposite the top, the first interior sterilization indicator being visible from the exterior of the pouch when viewed from the top of the pouch and through the first layer.

8. The sterilization pouch of claim 1 further comprising a top, a bottom opposite the top, and a first exterior sterilization indicator disposed on the bottom exterior surface of the second layer, the first interior sterilization indicator being visible from the exterior of the pouch when viewed from the top of the pouch and through the first layer of the pouch, and the first exterior sterilization indicator being visible from the exterior of the pouch when viewed from the bottom of the pouch.

9. The sterilization pouch of claim 1 further comprising barriers positioned interior to and adjacent the first indicator.

10. The sterilization pouch of claim 1 further comprising barriers positioned interior to and adjacent the first interior sterilization indicator and generally defining a discontinuous U shape.

11. The sterilization pouch of claim 6 further comprising barriers positioned interior to and adjacent the second interior sterilization indicator and generally defining a discontinuous U shape.

12. A sterilization pouch comprising:
a perimeter;
a first end;
a second end;
a length extending from the first end to the second end, the length having a major portion;
a first side;
a second side;
a width extending from the first side to the second side, the width having a major portion;
a first layer having a top exterior facing surface and a bottom interior facing surface;
a second layer bonded to the first layer along a portion of the perimeter so as to define a pouch having an opening and an interior space for receiving an article therein, the second layer having a top interior surface and a bottom exterior surface;
a first interior sterilization indicator that changes from a first color state to a second color state when exposed to a first sterilization condition, the first interior sterilization indicator
being disposed between the first layer and the second layer,
extending along the major portion of the length of the pouch and
extending along the major portion of the width of the pouch, and being visible through the first layer;
a second interior sterilization indicator that changes from a first color state to a second color state when exposed to a second sterilization condition,
the first and second interior sterilization indicators defining an arcuate pattern near the second end of the pouch; and
an arcuate barrier disposed interior to and adjacent the arcuate pattern of the second interior sterilization indicator.

13. A sterilization pouch comprising:
a perimeter;
a first end;
a second end;
a length extending from the first end to the second end, the length having a major portion;
a first side;
a second side;
a width extending from the first side to the second side, the width having a major portion;
a first layer having a top exterior facing surface and a bottom interior facing surface;
a second layer bonded to the first layer along a portion of the perimeter so as to define a pouch having an opening and an interior space for receiving an article therein, the second layer having a top interior surface and a bottom exterior surface;
a first interior sterilization indicator that changes from a first color state to a second color state when exposed to a first sterilization condition, the first interior sterilization indicator
being disposed between the first layer and the second layer,
extending along the major portion of the length of the pouch and
extending along the major portion of the width of the pouch, and being visible through the first layer;
a second interior sterilization indicator that changes from a first color state to a second color state when exposed to a second sterilization condition; and
barriers positioned interior to and adjacent the second interior sterilization indicator and generally defining a discontinuous U shape.

* * * * *